United States Patent
Buckberry (10) Patent No.: US 10,314,962 B2
(45) Date of Patent: Jun. 11, 2019

(54) RE-USE OF A HEMODIALYSIS CARTRIDGE

(71) Applicant: Quanta Fluid Solutions Ltd., Alcester, Warwickshire (GB)

(72) Inventor: Clive Henry Buckberry, Warwick (GB)

(73) Assignee: Quanta Dialysis Technologies Limited, Warwickshire (GB)

( * ) Notice: Subject to any disclaimer, the term of this patent is extended or adjusted under 35 U.S.C. 154(b) by 691 days.

(21) Appl. No.: 14/779,175

(22) PCT Filed: Mar. 27, 2014

(86) PCT No.: PCT/GB2014/050978
§ 371 (c)(1),
(2) Date: Sep. 22, 2015

(87) PCT Pub. No.: WO2014/155120
PCT Pub. Date: Oct. 2, 2014

(65) Prior Publication Data
US 2016/0051743 A1 Feb. 25, 2016

(30) Foreign Application Priority Data
Mar. 28, 2013 (GB) .................................. 1305755.9

(51) Int. Cl.
*A61M 1/16* (2006.01)
*A61M 1/34* (2006.01)

(52) U.S. Cl.
CPC ............ *A61M 1/169* (2013.01); *A61M 1/168* (2013.01); *A61M 1/1635* (2014.02);
(Continued)

(58) Field of Classification Search
CPC ........ A61M 1/169; A61M 1/34; A61M 1/168; A61M 1/1686; A61M 1/1635;
(Continued)

(56) References Cited

U.S. PATENT DOCUMENTS 3,753,493 A 8/1973 Mellor
4,666,598 A * 5/1987 Heath .................. A61M 1/3621
210/137

(Continued)

FOREIGN PATENT DOCUMENTS

EP 0754468 A2 1/1997
FR 2 310 136 3/1976

(Continued)

OTHER PUBLICATIONS

Sep. 29, 2015 International Preliminary Report on Patentability for PCT/GB2014/050978.

*Primary Examiner* — David C Mellon
(74) *Attorney, Agent, or Firm* — Hahn Loeser & Parks, LLP (57) ABSTRACT

The present invention provides a hemodialysis machine comprising a removably mountable cartridge having at least one inlet and at least one outlet, the cartridge defining a fluid pathway between said at least one inlet and said at least one outlet, a sanitisation device having an inlet and an outlet, a conduit connected between an outlet of the cartridge and the inlet of the sanitisation device and, a conduit connected between the outlet of the sanitisation device and an inlet of the cartridge.

5 Claims, 6 Drawing Sheets

(52) U.S. Cl.
CPC ............ *A61M 1/1686* (2013.01); *A61M 1/34* (2013.01); *A61M 2205/12* (2013.01); *A61M 2205/123* (2013.01); *A61M 2205/128* (2013.01)

(58) Field of Classification Search
CPC ........ A61M 2205/128; A61M 2205/12; A61M 2205/123; A61M 2205/125; A61M 2205/126; A61M 2205/3324; A61M 2209/10; B01D 61/24; B01D 61/243; B01D 61/30; B01D 61/32; B01D 65/02; B01D 65/022; B01D 65/06; B01D 2321/20; B01D 2321/2066; B01D 2321/2083

See application file for complete search history.

(56) References Cited

U.S. PATENT DOCUMENTS

| | | | |
|---|---|---|---|
| 5,304,349 A | | 4/1994 | Polaschegg |
| 5,591,344 A | * | 1/1997 | Kenley .................... A61L 2/04 210/636 |
| 5,650,071 A | * | 7/1997 | Brugger .............. A61M 1/3643 210/646 |
| 2009/0012450 A1 | | 1/2009 | Shah et al. |
| 2012/0269907 A1 | * | 10/2012 | Coates ................ A61M 1/1656 424/717 |

FOREIGN PATENT DOCUMENTS

| | | |
|---|---|---|
| WO | WO 96/25214 | 8/1996 |
| WO | WO 05/044339 A2 | 5/2005 |

\* cited by examiner

RE-USE OF A HEMODIALYSIS CARTRIDGE

The present application is a 35 USC § 371 submission of international application no. PCT/GB2014/050978, filed on 27 Mar. 2014 and published in the English language on 2 Oct. 2014 with publication no. WO 2014/155120 A1, which claims the benefit of the filing date of application no. GB 1305755.9, filed 28 Mar. 2013.

The present invention relates to dialysis machines and in particular, but not exclusively to a disposable cartridge for use in hemodialysis machines.

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis.

In peritoneal dialysis treatment, a dialysate solution is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to hemodialysis at a later stage.

In hemodialysis, the patient's blood is removed from the body by an arterial line and treated by a dialysis machine before being returned to the patient's body by a venous line. The machine passes the blood through a dialyser containing tubes formed from a semi-permeable membrane. On the exterior of the semi-permeable membrane is a dialysate solution. The semi-permeable membrane filters the waste products and excess fluid from the blood into the dialysate solution. The membrane allows the waste and a controlled volume of fluid to permeate into the dialysate solution whilst preventing the loss of larger more desirable molecules, like blood cells and certain proteins and polypeptides.

The action of dialysis across the membrane is achieved primarily by diffusion (the migration of molecules by random motion from a region of higher concentration to a region of lower concentration).

Fluid removal (otherwise known as ultrafiltration) is achieved by altering the hydrostatic pressure of the dialysate solution side of the membrane, causing free water to move across the membrane along the pressure gradient.

The correction of uremic acidosis of the blood is achieved by use of a bicarbonate buffer. The bicarbonate buffer also allows the correction of the blood bicarbonate level.

The dialysate solution consists of a sterilized solution of mineral ions. These ions are contained within an acid buffer which is mixed with the sterilised water and bicarbonate base prior to delivery to the dialyser.

Hemodialysis machines need to be sanitised between uses and maintained in a sanitised condition. Conventionally, known hemodialysis machines are sanitised either through heat cleaning or chemical cleaning to remove trace elements of dialysate solution from within fluid pathways defined by the hemodialysis machine. Dialysate solution comprises sodium bicarbonate as a constituent part which, if left in the hemodialysis machine, provides a natural food source for biofilm. Growth of biofilm in the fluid pathways defined by the hemodialysis machine can lead to unacceptable bio-incompatibility and errors in the hemodialysis process.

Conventional hemodialysis machines use peristaltic pumps, or similar, to flush a cleaning liquid through the hemodialysis machine in a single direction. Such machines risk contamination and growth of biofilm in areas of the machine where the cleaning liquid cannot access.

The present invention seeks to provide an improved hemodialysis machine.

A first aspect of the invention provides a hemodialysis machine comprising a removably mountable cartridge having a first inlet and a first outlet, the cartridge defining a fluid pathway therebetween, a sanitisation device having an inlet and an outlet, a conduit connected between the first outlet of the cartridge and the inlet of the sanitisation device, and, a conduit connected between the outlet of the sanitisation device and the first inlet of the cartridge.

Advantageously, provision of a sanitisation device permits the cartridge to be sanitised and re-used rather than being disposed of after each dialysis sitting.

Preferably, the cartridge further comprises a first mixing chamber, a second mixing chamber connected to the first mixing chamber, a first flow balance chamber connected to the second mixing chamber, a second flow balance chamber connected to the first flow balance chamber, wherein the sanitisation device is removably connected external to the cartridge between the first mixing chamber and the first flow balance chamber.

In one embodiment the cartridge further comprises a first inlet, a conduit between the first inlet of the cartridge and the first mixing chamber, a second inlet, a conduit between the second inlet of the cartridge and the first mixing chamber, a third inlet, a conduit between the third inlet of the cartridge and the second mixing chamber, a fourth inlet, a conduit between the fourth inlet of the cartridge and the second flow balance chamber, a first outlet, a conduit between the first inlet and the first outlet, a second outlet, a conduit between the first flow balance chamber and the second outlet, a third outlet, and, a conduit between the second flow balance chamber and the third outlet.

In one embodiment the sanitisation device comprises a chemical cleaning receptacle.

Preferably, the cleaning receptacle of one embodiment of the invention contains an acid concentrate.

In one embodiment, the chemical cleaning receptacle comprises a chemical bath.

In another embodiment, the chemical cleaning receptacle comprises a common manifold.

A second aspect of the invention provides a method of cleaning a cartridge for re-use in a hemodialysis machine comprising:
a) Providing a cartridge having at least one inlet and at least one outlet;
b) Connecting a sanitisation device between said at least one inlet and said at least one outlet of the cartridge external to the cartridge;
c) Flowing a liquid through the cartridge and the sanitisation device in a first direction;
d) Flowing the liquid through the cartridge and the sanitisation device in a second direction;
e) Flushing the liquid out of the cartridge through the at least one outlet.

Advantageously, directing a liquid through the cartridge in first and second directions is more efficient at sanitising the cartridge than directing the liquid through the cartridge in only one direction.

Preferably, the at least one inlet of the cartridge is a spent dialysate inlet and the at least one outlet is a drain port. In one embodiment, the cartridge further comprises a clean dialysate outlet, a water inlet, a water outlet, a bicarbonate inlet and an acid inlet.

In one embodiment, the method further comprises:
f) Connecting the spent dialysate solution inlet to the clean dialysate solution outlet;
g) Connecting the water outlet to the bicarbonate inlet;
h) Disconnecting the drain port;
i) Connecting the water inlet to a purified water supply;
j) Flushing purified water through the cartridge and out of the drain port and the acid inlet;
k) Connecting the drain port to the acid inlet;
l) Connecting the sanitisation device between the spent dialysate solution inlet and the clean dialysate outlet;
m) Measuring the conductivity of the liquid in the cartridge when flowing in a first direction to ensure that it indicates acid;
n) Disconnecting the sanitisation device and re-connecting the spent dialysate solution inlet to the clean dialysate solution outlet;
o) Flushing purified water through the cartridge and out of the drain port and the acid inlet;
p) Measuring the conductivity of the liquid in the cartridge to ensure that it indicates purified water;
q) Disconnecting all cartridge ports; and,
r) Connecting the cartridge 30 to the hemodialysis machine.

In another embodiment, the method further comprises:
f) Connecting the spent dialysate solution inlet, clean dialysate solution outlet, bicarbonate inlet, acid inlet and water outlet to a sanitisation device;
g) Connecting the water inlet to a purified water supply;
h) Connecting the drain port to a drain;
i) Flushing purified water through the cartridge and out of the drain port;
j) Measuring the conductivity of the liquid in the cartridge to ensure that it indicates acid;
k) Flushing purified water through the cartridge and out of the drain port;
l) Measuring the conductivity of the liquid in the cartridge to ensure that it indicates purified water;
m) Disconnecting all cartridge ports; and,
n) Connecting the cartridge to the hemodialysis machine.

In one embodiment, the method further comprises:
(f) Connecting a dialyser between the at least one inlet and the at least one outlet
(g) Connecting the dialyser to a blood pump Preferably, the at least one outlet is a dialysate solution outlet and the at least one outlet is a dialysate solution inlet.

Advantageously, the cleaning liquid as it flows through the cartridge, in a first direction and in a second direction, also flows through the dialyser and the blood pump to permit re-use of said dialyser and blood pump. The dialyser comprises a semi-permeable membrane which separates a dialysate solution circuit, defined by the cartridge, from a blood circuit, defined by the blood pump. The cleaning liquid permeates through the semi-permeable membrane from the dialysate solution circuit into the blood circuit and is flushed through the cartridge, the dialyser and the blood pump in first and second directions.

In one embodiment, the cartridge comprises at least two inlets and at least two outlets.

In another embodiment, the sanitisation device is connected between one of said at least inlets and one of said at least one outlets and the dialyser is connected between another of said at least one inlets and said at least one outlets.

An embodiment of the invention will now be described, by way of example only, with reference to the following figures.

Figure 1:
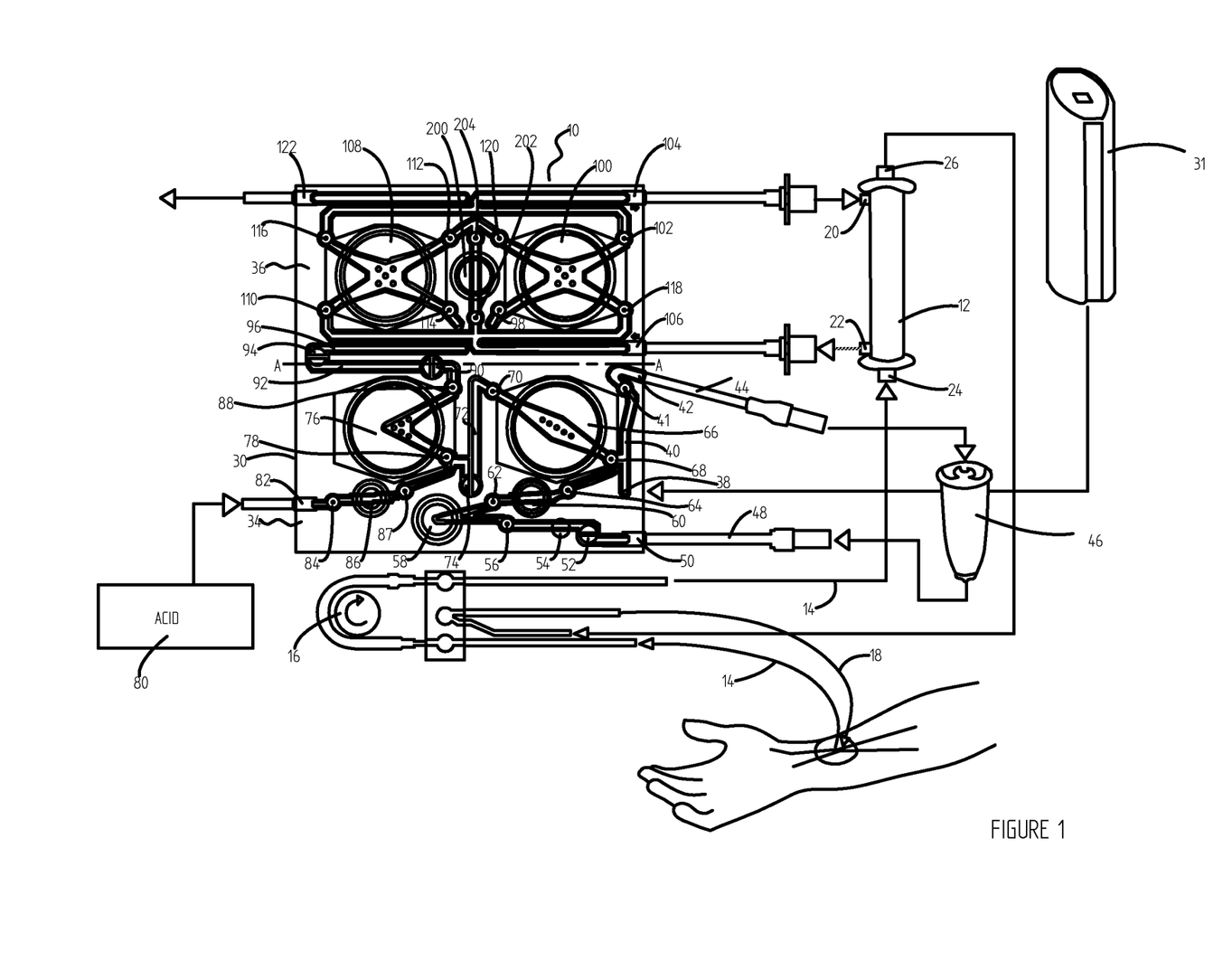
FIG. 1 shows a schematic of a dialysis system having a disposable cartridge comprising a fluid path defined by pumps and valves.
Figure 1A:
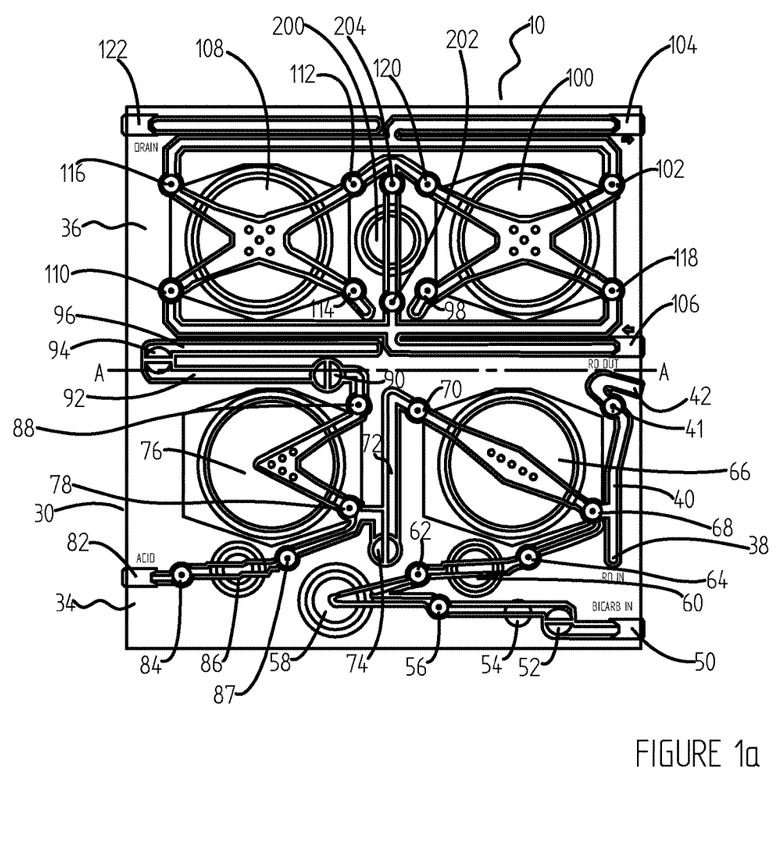
FIG. 1a shows a detailed schematic view of the cartridge of FIG. 1.

Referring to FIGS. 1 and 1a, a dialysis system, generally referred to as 10, is shown. A dialyser 12 receives blood via an arterial line 14 connected to a patient by a vascular access device (not shown for clarity), for example a hollow needle as typically used for drawing blood from a patient. The blood is pumped from the patient to the dialyser by a peristaltic pump 16. The blood passes through the dialyser in a known manner and is returned to the patient via a venous line 18. The dialyser 12 comprises a cylindrical tube closed by opposing ends. A semi-permeable membrane (not shown) is provided within the dialyser tube and separates the patients blood from a dialysate solution. The membrane extends substantially between the opposing ends of the cylinder. The dialysate solution removes impurities from the patients blood in a known manner.

The dialyser has an inlet 20 for receiving clean dialysate solution and an outlet 22 for removing spent dialysate solution from the dialyser 12. The dialyser also has an inlet 24 for receiving untreated blood from the peristaltic pump 16 and an outlet 26 for returning processed blood to the patient. The dialyser 12 is typically provided in a substantially upright orientation, in use, with the patients blood flowing longitudinally through the dialyser 12 from the blood inlet 24 to the blood outlet 26. The dialysate solution inlet 20 and dialysate solution outlet 22 are configured to be orientated substantially orthogonal to the blood inlet 24 and blood outlet 26, and to provide a counter-flow. Dialysate solution is circulated through the hemodialysis machine at a fluid flow rate in the region of 400 ml/min for approximately four hours.

The dialysis system defines a fluid circuit including a cartridge 30 as will now be described. The cartridge 30 is a consumable component in the hemodialysis machine described.

The cartridge 30 is formed from an acrylic plastic such as SG-10 and has a machine side and a patient side. The cartridge 30 defines pump chambers which are closed by respective diaphragms, formed from, for example, DEHP-free PVC, to define respective pumps. In this embodiment, each diaphragm is part of a single, common sheet of material applied to the machine side of the cartridge 30. The individual diaphragms are operable by pneumatic pressure applied thereto.

A series of flow paths are formed in the cartridge 30 for carrying dialysate solution constituted from water, bicarbonate solution and acid solution. The flow paths are located between the sheet of material closing the machine side of the cartridge 30 and a further sheet of the same material closing the patient side of the cartridge 30.

In use, the variation of pressure applied to the flexible diaphragm of each pump chamber is controlled by conventional valving. A pressure source applies either a positive or negative pressure to one side of the diaphragm of each pump chamber, as required, to pump fluid through the fluid paths in the cartridge 30, in a circuit defined by a plurality of valves.

The valves of the cartridge 30 are conventional diaphragm valves defined by respective openings in the cartridge 30 and closed by respective flexible diaphragms. Each valve is operable by applying a negative pressure to the diaphragm to open the valve and applying a positive pressure to the diaphragm to close the valve. The diaphragm of each valve is part of the single, common sheet of material applied to the machine side of the cartridge 30. The valves are opened and closed according to a flow control strategy, as will become apparent.

The machine side of the cartridge 30 abuts a pump driver (not shown) comprising a platen having a plurality of recessed surfaces, each recessed surface substantially corresponding in geometry and volume to a pump chamber defined in the cartridge 30. Each recessed surface has a fluid port connectable with a source of positive fluid pressure and, with a source of negative fluid pressure via a valve.

The positive and negative fluid pressure sources include a pressure pump and a vacuum pump respectively. When the valve is operated to allow fluid to flow into a recessed surface from the source of positive fluid pressure, the diaphragm moves into a corresponding pump chamber and any fluid, i.e. dialysate solution, therein is expelled from that pump chamber via the series of flow paths. When the valve is operated to allow fluid to flow out of a recessed surface to the source of negative fluid pressure, the diaphragm is moved away from a pump chamber and into the corresponding recessed surface to permit fluid to be drawn into that pump chamber via the series of flow paths. The surface of the pump chambers and of the platen provide a positive stop for each diaphragm, to prevent overstretching thereof. The positive stop ensures that the volume of fluid drawn into and pumped from the pump chambers is accurately controlled.

Figure 2:
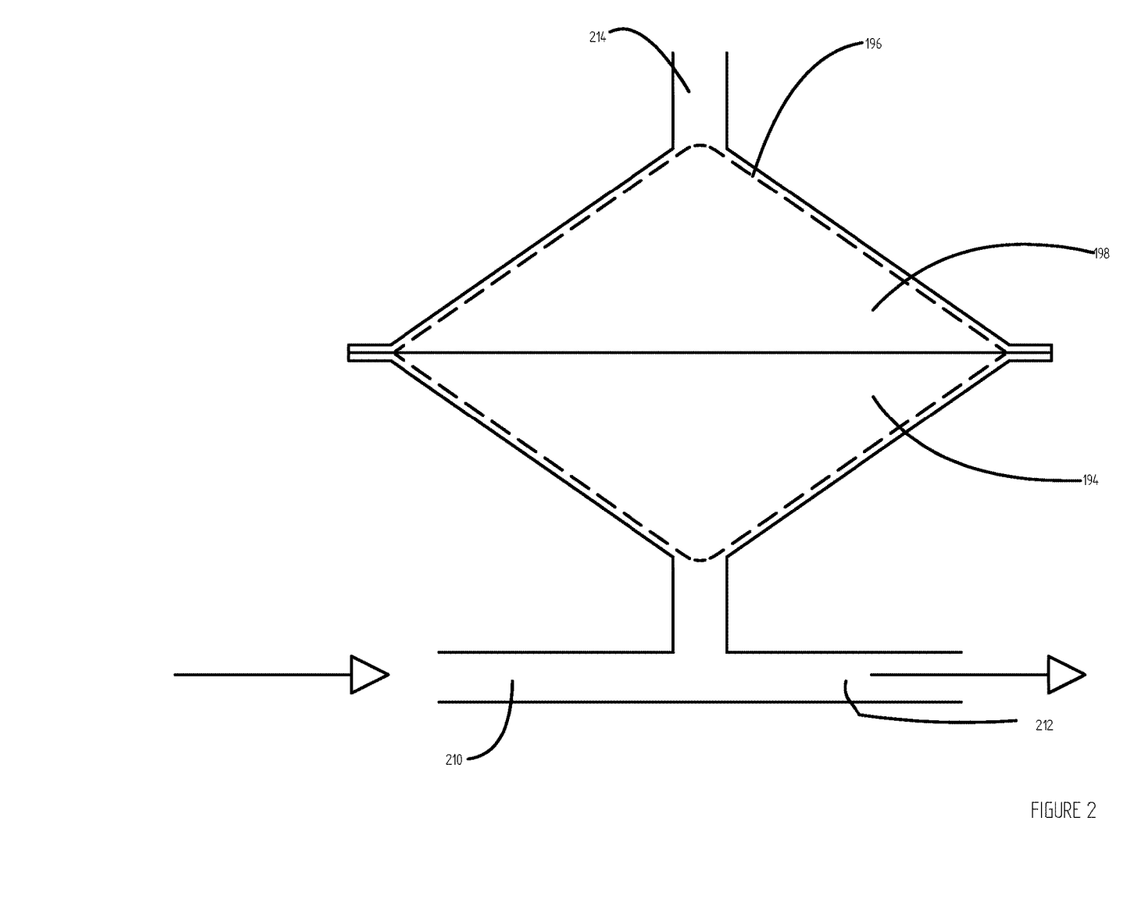
FIG. 2 shows a schematic view of the operation of a pump of the type defined by the disposable cartridge.
Figure 3A:
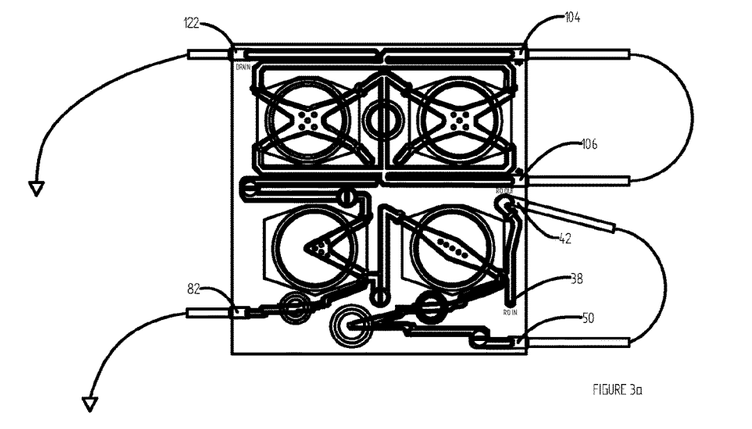
FIGS. 3a to 3d show schematic views of a first method of sanitising the disposable cartridge of an embodiment of the invention.
Figure 3B:
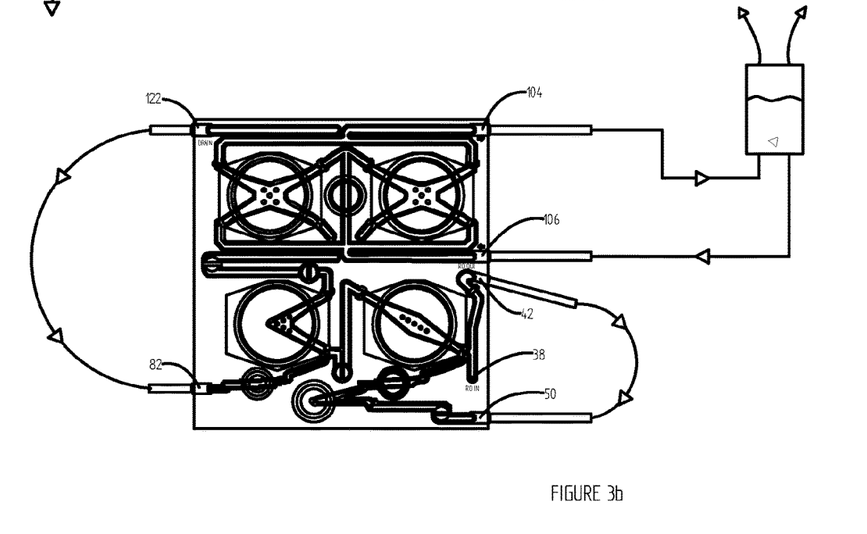
Figure 3C:
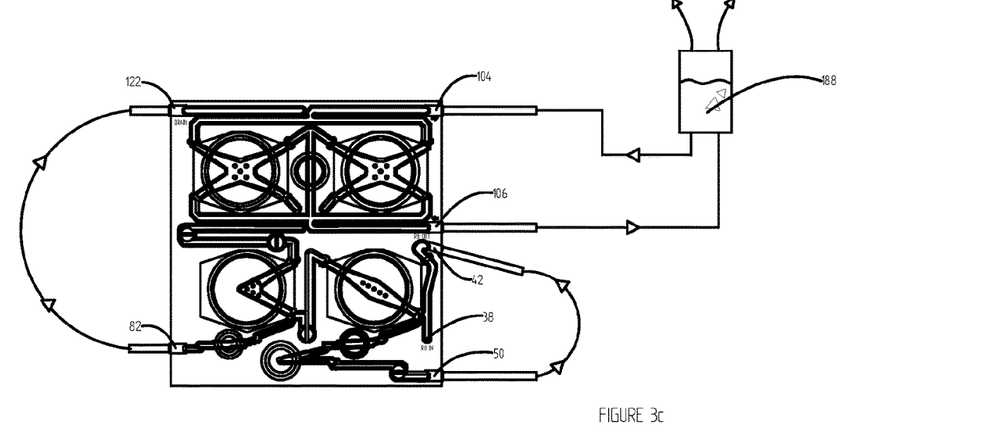
Figure 3D:
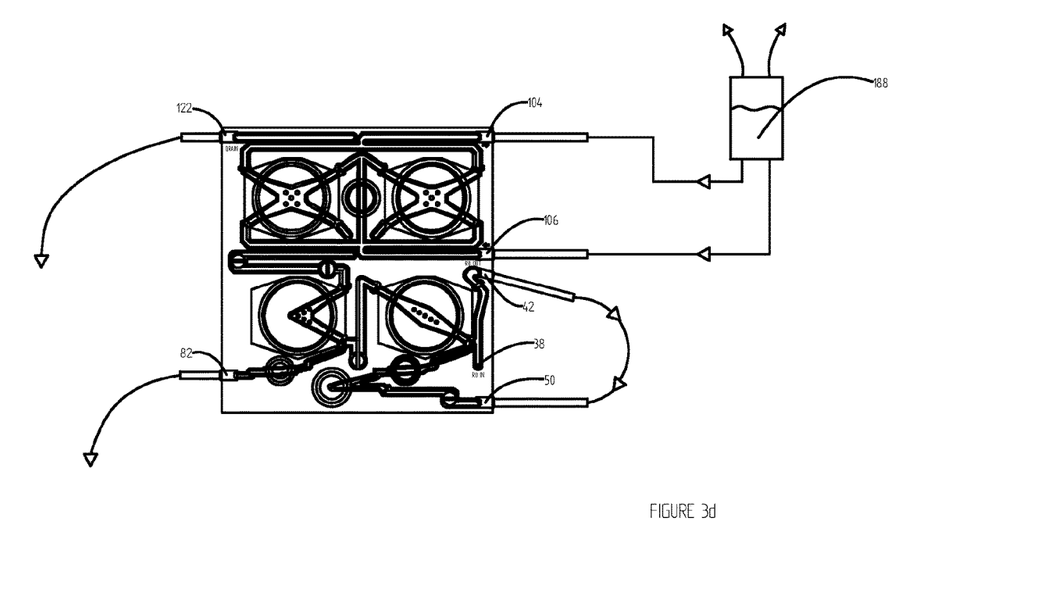

The cartridge 30 has two main functions, preparation of dialysate solution and flow balance. Each function is performed by a separate part of the cartridge as illustrated in FIGS. 1 and 2 by the schematic separation of the cartridge into two parts by the line A-A in the figures. The dialysate preparation function is performed by one part of the cartridge, generally referred to at 34 and the flow balance function is performed by the other part of the cartridge, generally referred to at 36. The cartridge 30 prepares an accurately mixed homogenous dialysate solution and ensures that the flow of clean dialysate supplied to the dialyser 12 matches (to within clinical tolerances) the volume of spent dialysate drawn from the dialyser 12.

The cartridge 30 is provided with a plurality of connections to and from the cartridge 30 as described below.

A first inlet port 38, from hereon referred to as the water inlet port, defined in the machine side of the cartridge 30 receives purified water from a purified water supply 31 such as a reverse osmosis water supply.

A first outlet port 42, from hereon referred to as the water outlet port, defined in an edge of the cartridge 30 directs the purified water to a first dialysate solution constituent which, in the illustrated embodiment shown in FIGS. 1 and 1a, is bicarbonate 46.

A second inlet port 50, from hereon referred to as the bicarbonate inlet port, defined in the same edge of the cartridge 30 as the water outlet port 42 receives purified water mixed with the bicarbonate 46.

A third inlet port 82, from hereon referred to as the acid inlet port, defined in the opposite edge of the cartridge 30 to the water outlet port 42 and bicarbonate inlet port 50 receives a second dialysate solution constituent which, in the illustrated embodiment shown in FIGS. 1 and 1a, is acid 80.

A second outlet port 104, from hereon referred to as the clean dialysate solution outlet port, is defined in the same edge of the cartridge as the water outlet port 42 and the bicarbonate inlet port 50. The clean dialysate outlet port 104 directs clean dialysate solution to the dialyser 12.

A fourth inlet port 106, from hereon referred to as the spent dialysate solution inlet port, is defined in the same edge of the cartridge 30 as the water outlet port 42, bicarbonate inlet port 50 and clean dialysate outlet port 104. The spent dialysate solution inlet port 106 receives spent dialysate solution from the dialyser 12.

A third outlet port 122, from hereon referred to as the drain port, is defined in the same edge of the cartridge as the acid inlet port 82. The drain port 122 directs spent dialysate solution out of the cartridge 30.

Dialysate Preparation

Dialysate solution is prepared in the cartridge 30 by combining purified water with two dialysate constituents, namely a bicarbonate solution and an acid solution.

Purified water is admitted into the cartridge 30 from a purified water supply 31 via the water inlet port 38. The purified water passes through a channel 40 via a water inlet valve 41, when open, and exits the cartridge 30 at the water outlet port 42. From here, the purified water is carried by a tube 44 through a bicarbonate cartridge 46 in a known manner to generate a purified water and bicarbonate solution. The purified water and bicarbonate solution is carried by a tube 48 and re-admitted into the cartridge 30 via the bicarbonate inlet port 50.

The temperature of the bicarbonate solution is measured at sensing port 52 and the bicarbonate solution pressure is measured at sensing port 54. The bicarbonate solution passes a bicarbonate control valve 56, when open, before entering a bicarbonate solution reservoir 58 having an inlet and an outlet. The bicarbonate control valve 56 is closed when flow therethrough is not required.

A bicarbonate dosing pump chamber 60 having an inlet and an outlet receives the bicarbonate solution from the bicarbonate solution reservoir 58 through a bicarbonate dosing pump inlet valve 62. The bicarbonate dosing pump chamber 60 is closed by a diaphragm to define a bicarbonate dosing pump which, upon actuation of the diaphragm, pumps the bicarbonate solution from the bicarbonate dosing pump 60 to a first mixing pump chamber 66 (bicarbonate pump chamber). The bicarbonate dosing pump 60 has a bicarbonate dosing pump outlet valve 64 which is closed when the bicarbonate dosing pump inlet valve 62 is open. The bicarbonate dosing pump outlet valve 64 is opened to permit bicarbonate solution to be pumped to the bicarbonate pump chamber 66. When the bicarbonate dosing pump outlet valve 64 is open, the bicarbonate dosing pump inlet valve 62 is closed to prevent bicarbonate solution from being pumped back into the bicarbonate solution reservoir 58.

The bicarbonate pump chamber 66 having an inlet and an outlet receives the purified water and bicarbonate solution from the bicarbonate dosing pump 60 via a bicarbonate pump inlet valve 68. The bicarbonate pump inlet valve 68, when open, can also admit purified water into the bicarbonate pump chamber 66 from the water inlet port 38. The bicarbonate pump chamber 66 is closed by a diaphragm to define a pump which, upon actuation of the diaphragm, pumps the bicarbonate solution and purified water therein through a bicarbonate pump outlet valve 70 to a second mixing pump chamber 76 (acid pump).

When the bicarbonate pump inlet valve 68 is open, the bicarbonate pump outlet valve 70 and water outlet valve 41 are closed. When the bicarbonate pump outlet valve 70 is open, the bicarbonate pump inlet valve 68 is closed to prevent the bicarbonate and purified water solution from being pumped back into channel 40.

From the bicarbonate pump outlet valve 70, the bicarbonate and purified water solution enters a sensor channel 72 in which the hemodialysis machine measures the conductivity of the bicarbonate and purified water solution in a known manner. The bicarbonate and purified water solution then enters a temperature sensor 74 before, if the conductivity and temperature of the bicarbonate and purified water solution are within tolerance, entering the acid pump chamber 76.

The acid pump chamber 76 having an inlet and an outlet receives the bicarbonate and purified water solution from the bicarbonate pump 66 via an acid pump inlet valve 78. The acid pump inlet valve 78, when open, can also admit an acid solution into the pump chamber 76. The acid pump chamber 76 is closed by a diaphragm to define a pump which, upon actuation of the diaphragm, pumps the acid solution, bicarbonate solution and purified water therein through an acid pump outlet valve 88 to the first flow balance pump chamber 100. When the acid pump inlet valve 78 is open, the acid pump outlet valve 88 is closed. When the acid pump outlet valve 88 is open, the acid pump inlet valve 78 is closed.

The acid solution is admitted into the cartridge 30 from a pre-determined supply of acid 80 via the acid solution inlet port 82. From the acid solution inlet port the acid solution passes through an acid dosing pump chamber 86 via an acid dosing pump inlet valve 84 and an acid dosing pump outlet valve 87. The acid dosing pump outlet valve 87 is closed when the acid dosing pump inlet valve 84 is open. The acid dosing pump inlet valve 84 is closed when the acid dosing pump outlet valve 87 is open.

The dialysate solution exits the acid pump chamber via the acid pump outlet valve 88 and passes through a first dialysate solution temperature sensor 90 and a first dialysate solution conductivity sensor 92. A second dialysate solution temperature sensor 94 and a second dialysate solution conductivity sensor 96 are provided to corroborate the data provided by the first dialysate solution temperature sensor 90 and the first dialysate solution conductivity sensor 92. Providing the data measured by sensors 90, 92, 94 and 96 is within tolerance, the dialysate solution is admitted into a first flow balance pump chamber 100

Flow Balance

The flow balance function of the cartridge 30 provides first and second flow balance pump chambers 100, 108, each having two inlets and two outlets to define two independent flow paths therethrough. The first and second flow balance pump chambers 100, 108 are of approximately equal volume. Either the first or second flow balance pump chamber 100, 108 pumps dialysate solution to a dialyser 12 and the other of the first or second flow balance pump chambers 100, 108 pumps dialysate solution from the dialyser 12 to the drain port 122. After every approximately 20 strokes of the first and second flow balance pumps 100, 108, their function is reversed.

From this point onwards, dialysate solution will be referred to as either clean dialysate solution or spent dialysate solution. Clean dialysate solution is intended to mean dialysate solution that is either new dialysate solution or clean dialysate solution that has been treated to remove waste product therefrom. Spent dialysate solution is intended to mean dialysate solution that has passed through the dialyser 12 to remove waste fluids from a patients blood into the dialysate solution.

Each of the first and second flow balance pump chambers 100, 108 are closed by a diaphragm to define respective pumps. The diaphragm is actuated away from a pump chamber by a negative pressure source to draw a volumetrically measured quantity of dialysate solution into the pump chamber. The diaphragm is actuated toward the pump chamber to pump the fluid therein out of an outlet.

The first flow balance pump chamber 100 has a clean dialysate solution inlet valve 98 for receiving clean dialysate solution from the acid pump 76 and a clean dialysate solution outlet valve 102 for pumping clean dialysate solution to the dialyser 12. The first flow balance pump chamber 100 also has a spent dialysate solution inlet valve 118 for receiving spent dialysate solution from the dialyser 12 and a spent dialysate solution outlet valve 120 for pumping the spent dialysate to drain via drain outlet port 122.

At any one time, only one of valves 98, 102, 118 or 120 will be open and the other three valves will be closed. The flow balance function, as described above, requires alternating the function of each flow balance pump approximately every 20 cycles. Therefore, when the first flow balance pump 100 is pumping clean dialysate solution to the dialyser 12, only valves 98 and 102 are in use and when the first flow balance pump 100 is pumping spent dialysate solution from the dialyser 12 to drain, only valves 118 and 120 will be in use.

The clean dialysate solution is pumped out of the first flow balance pump chamber 100 through the first flow balance pump clean dialysate solution outlet valve 102, upon closure of the first flow balance pump clean dialysate inlet valve 98, to the dialyser 12 via the dialyser outlet port 104.

Spent dialysate solution returns to the cartridge 30 from the dialyser 12 via the dialyser inlet port 106. The second flow balance pump chamber 108 has a spent dialysate solution inlet valve 110 for receiving spent dialysate solution from the dialyser 12 and a spent dialysate solution outlet valve 112 for pumping the spent dialysate solution to drain via drain outlet port 122. The second flow balance pump 108 also has a clean dialysate solution inlet valve 114 for receiving clean dialysate solution from the acid pump chamber 76 and a clean dialysate solution outlet valve 116 for pumping clean dialysate solution to the dialyser 12.

At any one time, only one of valves 110, 112, 114, 116 will be open and the other three valves will be closed. When the second flow balance pump 108 is pumping clean dialysate solution to the dialyser 12, only valves 114 and 116 will be in use and when the second flow balance pump 108 is pumping spent dialysate solution from the dialyser 12 to drain, only valves 114 and 116 will be in use.

In the illustrated example, the operation of the first and second flow balance pumps 100, 108 can be switched so that the first flow balance pump 100 is used to draw spent dialysate solution from the dialyser 12 and the second flow balance pump 108 is used to pump clean dialysate solution into the dialyser 12 as described below.

The clean dialysate solution is drawn into the second flow balance pump chamber 108 from the acid pump 76 via the second flow balance pump clean dialysate solution inlet valve 114 upon actuation of the diaphragm. The clean dialysate solution is then pumped from the second flow balance pump chamber 108 via the second flow balance pump clean dialysate solution outlet valve 116, upon closure of the clean dialysate solution inlet valve 114, to the dialyser 12.

Spent dialysate solution from the dialyser 12 is drawn into the first flow balance pump 100 via the second flow balance pump spent dialysate solution inlet valve 118. The spent dialysate solution is then pumped out of the first flow balance pump chamber 100 via the second flow balance pump spent dialysate solution outlet valve 120, upon closure of the spent dialysate solution inlet valve 118, to drain via drain outlet port 122.

The volume of fluid that is returned from the dialyser 12 is greater than the volume of fluid that is pumped to the dialyser via the first or second flow balance pump 100, 108. The first and second flow balance pumps have fixed volumes meaning that the excess fluid volume cannot be accommodated in the first or second flow balance pump. An ultrafiltration pump 200 is provided between the first and second flow balance pumps 100, 108 and has an inlet valve 210 and an outlet valve 212. The ultrafiltration pump 200 comprises a concave recess in the cartridge closed by a flexible diaphragm, the concave recess and the flexible diaphragm defining an ultrafiltration pump chamber.

In use, the inlet valve 210 of the ultrafiltration pump 200 is opened to allow the ultrafiltration pump to draw in a pre-determined volume of spent dialysate solution. When the inlet valve 210 of the ultrafiltration pump is open, the outlet valve 212 of the ultrafiltration pump 200 is closed. When the ultrafiltration pump 200 has received a volume of spent dialysate solution, the outlet valve 212 is opened and the spent dialysate solution in the ultrafiltration pump chamber is pumped through the outlet valve 212 to drain via the drain outlet port 122. When the outlet valve 212 of the ultrafiltration pump 200 is open, the inlet valve 210 of the ultrafiltration pump 200 is closed.

FIG. 2 shows a representative view of a flow balance pump 100 according to the present invention. The flow balance pump chamber 194 is provided on the cartridge and is closed by a diaphragm 196 which, at rest, sits across the pump chamber 194. The pump chamber receives either clean or spent dialysate solution via a dialysate solution inlet port 210 and pumps dialysate solution from the pump chamber via a dialysate solution outlet port 212.

The cartridge 30 is removably mounted into a hemodialysis machine which has a flow balance pump cavity 198 substantially corresponding in dimension and shape to the pump chamber 194. Upon supply of positive or negative pressure via a pump cavity pressure inlet port 214, the diaphragm is actuated into either the pump chamber 194 or pump cavity 198 to either draw fluid into the pump chamber 194 or pump fluid from the pump chamber 194.

Cartridge Cleaning

After each use, the hemodialysis machine requires sanitising to prevent contamination of a patients bloodstream during subsequent dialysis sittings. The removable cartridge 30, as described above, is usually disposed of after each sitting. In one embodiment of the invention, the cartridge 30 is sanitised to allow re-use in subsequent dialysis sittings.

A sanitisation device 188, such as a chemical cleaning receptacle, is connected to the cartridge 30 using the following method (see FIGS. 3a to 3d):

a) Connecting the spent dialysate solution inlet 104 to the clean dialysate solution outlet 106;
b) Connecting the water outlet 42 to the bicarbonate inlet 50;
c) Disconnecting the drain port 122;
d) Connecting the water inlet 38 to a purified water supply 31;
e) Flushing purified water through the cartridge 30 and out of the drain port 122 and out of the acid inlet 82;
f) Connecting the drain port 122 to the acid inlet 82;
g) Connecting a sanitisation device 188 between the spent dialysate solution inlet 104 and the clean dialysate solution outlet 106;
h) Flowing a liquid through the cartridge and the sanitisation device in a first direction;
i) Flowing the liquid through the cartridge 30 in a second direction;
j) Disconnecting the sanitisation device 188 and re-connecting the spent dialysate solution inlet 104 to the clean dialysate solution outlet 106;
k) Flushing purified water through the cartridge 30 and out of the drain port 122 and the acid inlet 82;
l) Disconnecting all cartridge ports 104, 106, 42, 38, 122; and,
m) Re-connecting the cartridge 30 to the hemodialysis machine 10.

Figure 4:
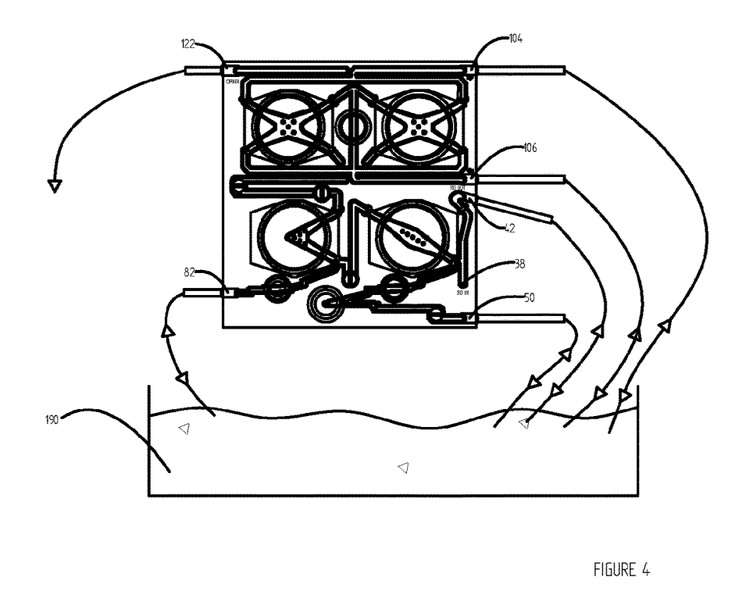
FIG. 4 shows a schematic view of a second method of sanitising the disposable cartridge of an embodiment of the invention.

An alternative method of cleaning the cartridge provides (See FIG. 4):

a) Connecting the spent dialysate solution inlet 104, clean dialysate solution outlet 106, bicarbonate inlet 50, acid inlet 82 and water outlet 42 to a chemical bath 190;
b) Connecting the water inlet 38 to a purified water supply 31;
c) Connecting the drain port 122 to a drain;
d) Flushing purified water through the cartridge 30 and out of the drain port 122;
e) Flowing a cleaning chemical from the chemical bath 190 through the cartridge 130 in a first direction;
f) Measuring the conductivity level of the chemical to ensure that it indicates acid;
g) Flowing the chemical from the chemical bath 190 through the cartridge 30 in a second direction;
h) Flushing purified water through the cartridge 30 and out of the drain port 122;
i) Measuring the conductivity of the purified water to ensure that it indicates purified water;
j) Disconnecting all cartridge ports 104, 106, 50, 82, 42, 38; and,
k) Re-connecting the cartridge 30 to the hemodialysis machine 10.

The chemical bath 190 may be provided with a heater to heat the cleaning chemical contained therein before the cleaning chemical is flowed through the cartridge 30.

Figure 5:
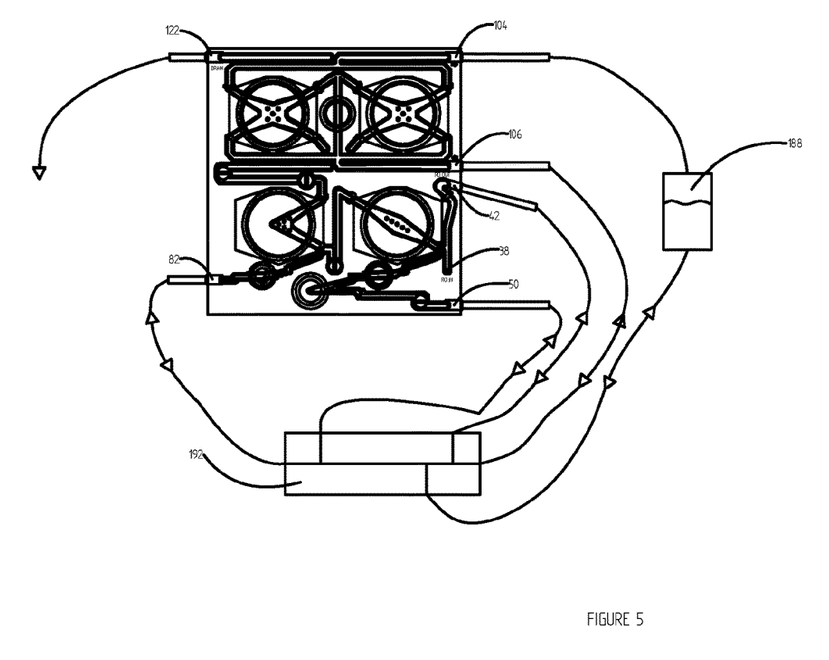
FIG. 5 shows a schematic view of a third method of sanitising the disposable cartridge of an embodiment of the invention.

In another alternative method, with reference to FIG. 5, the chemical bath 190 could be replaced by a manifold 192 with a chemical receptacle provided between the manifold and any one or more of the clean dialysate outlet, spent dialysate inlet, bicarbonate port, acid port and water outlet.

In any of the methods of cleaning the cartridge described, the cleaning chemical is drawn through the cartridge by one or more of the acid pump, bicarbonate pump, first flow balance pump or second flow balance pump.

The dialyser 12, if connected to the cartridge 30, can also be cleaned by the cleaning liquid to allow re-use for subsequent dialysis sessions. Cleaning fluid, when passing through the dialyser 12, permeates through the semi-permeable membrane of the dialyser 12 and enters a blood pump (not shown) connected to the dialyser 12. In this way, the membrane of the dialyser 12 and the blood pump are cleaned in the same manner as the cartridge 30.

The embodiments of the present invention, described with reference to the figures, are examples only and not exclude variations therefrom from the scope of the claims.

The invention claimed is:

1. A method of cleaning a dialysate mixing and flow balance cartridge for re-use in the hemodialysis machine, comprising:
   a) providing the cartridge, the cartridge having a first mixing pump chamber, a second mixing pump chamber connected to the first mixing pump chamber, a first flow balance pump chamber connected to the second mixing pump chamber, a second flow balance pump chamber, at least one inlet and at least one outlet;
   b) connecting a sanitisation device between the at least one inlet and the at least one outlet of the cartridge, the sanitisation device comprising a chemical cleaning receptacle that is external to the cartridge;
   c) flowing a liquid through the cartridge and the sanitisation device in a first direction by actuation of at least one of the pump chambers on the cartridge;
   d) flowing the liquid through the cartridge and the sanitisation device in a second direction by actuation of at least one of the pump chambers on the cartridge; and
   e) flowing the liquid out of the cartridge through the at least one outlet; and
   wherein the at least one inlet of the cartridge comprises a plurality of inlets, each one of a spent dialysate solution inlet, a water inlet, a bicarbonate inlet and an acid inlet being a respective one of the plurality of inlets; and
   the at least one outlet comprises a plurality of outlets, each one of a drain port, a clean dialysate solution outlet, and a water outlet being a respective one of the plurality of outlets.

2. The method of cleaning the cartridge for re-use in the hemodialysis machine according to claim 1, further comprising:
   f) connecting the spent dialysate solution inlet to the clean dialysate solution outlet;
   g) connecting the water outlet to the bicarbonate inlet;
   h) disconnecting the drain port;
   i) connecting the water inlet to a purified water supply;
   j) after performing the steps f through i, flushing purified water through the cartridge and out of the drain port and the acid inlet;
   k) then connecting the drain port to the acid inlet;
   l) then performing the step b connecting step by connecting the sanitisation device between the spent dialysate solution inlet and the clean dialysate solution outlet;
   m) after performing the step l and while performing the step c, measuring conductivity of the liquid in the cartridge when flowing in the first direction to confirm that the liquid in the cartridge is not purified water;
   n) after performing the steps m and d, disconnecting the sanitisation device, re-connecting the spent dialysate solution inlet to the clean dialysate solution outlet, and disconnecting the drain port from the acid inlet;
   o) then performing the step e flowing step by flushing purified water through the cartridge and out of the drain port and the acid inlet;
   p) then measuring the conductivity of the liquid in the cartridge to confirm that the liquid in the cartridge is purified water;
   q) then disconnecting all of the cartridge inlets and outlets; and
   r) then connecting the cartridge to the hemodialysis machine.

3. The method of cleaning the cartridge for re-use in the hemodialysis machine according to claim 1, further comprising:
   f) performing the step b connecting step by connecting the spent dialysate solution inlet, the clean dialysate solution outlet, the bicarbonate inlet, the acid inlet and the water outlet to the sanitisation device;
   g) connecting the water inlet to a purified water supply;
   h) connecting the drain port to a drain;
   i) after performing the steps f through h, flushing purified water through the cartridge and out of the drain port;
   j) then performing the step c by flowing a chemical from the sanitization device;
   k) after or while performing step j, measuring conductivity of the liquid in the cartridge to confirm that the liquid in the cartridge is not purified water;
   l) after performing the step k, performing the step e flowing step by flushing purified water through the cartridge and out of the drain port;
   m) then measuring the conductivity of the liquid in the cartridge to confirm that the liquid in the cartridge is purified water;
   n) then disconnecting all of the cartridge inlets and outlets; and
   o) then connecting the cartridge to the hemodialysis machine.

4. The method of cleaning the cartridge for re-use in the hemodialysis machine according to claim 1, wherein the spent dialysate solution inlet, the clean dialysate solution outlet, the bicarbonate inlet, the acid inlet and the water outlet are connected to the sanitisation device via a common manifold, the manifold having a single fluid path to the sanitisation device.

5. The method of cleaning the cartridge for re-use in the hemodialysis machine according to claim 1, wherein the spent dialysate solution inlet, the clean dialysate solution outlet, the bicarbonate inlet, the acid inlet and the water outlet each have a respective fluid path to the sanitisation device.

* * * * *